United States Patent
Yoo et al.

(10) Patent No.: US 7,989,197 B2
(45) Date of Patent: Aug. 2, 2011

(54) MICROFLUIDIC DEVICE INCLUDING A MICROCHANNEL WITH A HYDROPHOBIC POROUS POLYMER BONDED TO WALLS THEREOF AND TO A MAGNETIC BEAD, AND METHODS OF MAKING AND USING THE DEVICE

(75) Inventors: Chang-eun Yoo, Yongin-si (KR); Jong-myeon Park, Yongin-si (KR); Sung-young Jeong, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 1036 days.

(21) Appl. No.: 11/675,840

(22) Filed: Feb. 16, 2007

(65) Prior Publication Data
US 2008/0009043 A1 Jan. 10, 2008

(30) Foreign Application Priority Data
Jul. 5, 2006 (KR) .................. 10-2006-0062976

(51) Int. Cl.
*C12M 1/34* (2006.01)
(52) U.S. Cl. ............... 435/287.2; 435/288.5; 435/306.1; 422/502
(58) Field of Classification Search ............... 435/287.2, 435/288.5, 288.7, 288.6, 306.1; 422/502, 422/527, 535
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,965,188 A | 10/1990 | Mullis et al. |
| 5,283,079 A | 2/1994 | Wang et al. |
| 5,318,797 A | 6/1994 | Matijevic et al. |
| 5,395,688 A | 3/1995 | Wang et al. |
| 5,834,121 A | 11/1998 | Sucholeiki et al. |
| 2003/0040129 A1 | 2/2003 | Shah |
| 2003/0150739 A1 | 8/2003 | Morozov et al. |
| 2004/0018611 A1 | 1/2004 | Ward et al. |
| 2006/0110725 A1 | 5/2006 | Lee et al. |
| 2007/0035587 A1 | 2/2007 | Lee et al. |

FOREIGN PATENT DOCUMENTS

| | | |
|---|---|---|
| EP | 1662008 A2 | 5/2006 |
| EP | 1759759 A1 | 3/2007 |
| JP | 2005-218439 A | 8/2005 |
| WO | 0171311 A2 | 9/2001 |

OTHER PUBLICATIONS

Yogi, O., et al.; "On-Demand Droplet Spotter for Preparing Pico- to Femtoliter Droplets on Surfaces"; Anal. Chem.; vol. 73; pp. 1896-1902; 2001.

Moerman, R., et al.; "Miniaturized Electrospraying as a Technique for the Production of Microarrays of Reproducible Micrometer-Sized Protein Spots"; Anal. Chem.; vol. 73; pp. 2183-2189; 2001.

(Continued)

*Primary Examiner* — William H Beisner
(74) *Attorney, Agent, or Firm* — Cantor Colburn LLP (57) ABSTRACT

This invention provides a microfluidic device comprising an inlet and an outlet which are connected with each other through a microchannel, wherein a polymerized hydrophobic porous polymer is bonded to magnetic beads and to the walls of the microchannel. The invention is further directed to methods of making and using the microfluidic device.

17 Claims, 2 Drawing Sheets

OTHER PUBLICATIONS

Morozov, V.N., et al.; "Electrospray Deposition as a Method for Mass Fabrication of Mono- and Multicomponent Microarrays of Biological and Biologically Active Substances"; Anal. Chem.; vol. 71, No. 15; pp. 3110-3117; Aug. 1, 1999.

European Search Report dated Sep. 25, 2007 for Application No. 07107676.4.

Japanese Office Action mailed on Mar. 30, 2010.

Chinese Office Action mailed on Dec. 31, 2010 on Application No. 200710084331.8, with English Translation.

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Forward primer

<400> SEQUENCE: 1
tgtatgaaga aggcttcg                                                   18

<210> SEQ ID NO 2
<211> LENGTH: 19
<212> TYPE: DNA
<213> ORGANISM: Artificial Sequence
<220> FEATURE:
<223> OTHER INFORMATION: Reverse primer

<400> SEQUENCE: 2
aaaggtatta actttactc                                                  19

<210> SEQ ID NO 3
<211> LENGTH: 20
<212> TYPE: DNA
<213> ORGANISM: Artificial Sequence
<220> FEATURE:
<223> OTHER INFORMATION: Taqman probe

<400> SEQUENCE: 3
gtactttcag cggggaggaa                                                 20
```

MICROFLUIDIC DEVICE INCLUDING A MICROCHANNEL WITH A HYDROPHOBIC POROUS POLYMER BONDED TO WALLS THEREOF AND TO A MAGNETIC BEAD, AND METHODS OF MAKING AND USING THE DEVICE

This application claims priority to Korean Patent Application No. 10-2006-0062976, filed on Jul. 5, 2006, and all benefits accruing therefrom under 35 U.S.C. §119, the disclosure of which is incorporated herein in its entirety by reference.

BACKGROUND OF THE INVENTION

1. Field of the Invention

The present invention relates to a microfluidic device including a microchannel, wherein a hydrophobic porous polymer is bonded to walls of the microchannel, and a magnetic bead is bonded to the hydrophobic porous polymer. The present invention further relates to a method of concentrating cells, and extracting and amplifying DNA using the microfluidic device.

2. Description of the Related Art

Microfluidic devices are devices in which at least one inlet and outlet are connected through a microchannel. A microfluidic device is generally used as, for example, a lab-on-a-chip for cell concentrating, cell separating, cell disrupting and amplifying nucleic acid.

A magnetic bead is generally an encapsulated metal oxide particle comprised of a rigid polymeric coating encapsulating the metal oxide particle. The "metal oxide particle" refers to a particle comprising any oxide of a metal or metal alloy having paramagnetic or superparamagnetic properties. A paramagnetic particle refers to a metal oxide particle, which is susceptible to the application of external magnetic fields, yet is unable to maintain a permanent magnetic domain. Stated another way, a paramagnetic particle has inducible magnetic properties. The term "rigid" refers to a polymeric coating that is sufficiently cross linked to the extent that the polymeric coating encapsulates and stabilizes the metal oxide particle within the coating in a manner that the particle remains enclosed therein. Such magnetic beads can be manufactured using known methods in the field. For example, U.S. Pat. Nos. 5,395,688; 5,318,797; and 5,283,079 disclose various magnetic beads.

U.S. Pat. No. 5,834,121 discloses a composite magnetic bead comprising a) a microporous matrix of a first polymer comprising at least one vinyl monomer; and b) a plurality of primary beads, wherein each primary bead comprises a metal oxide having inducible magnetic properties and a coating of a second polymer that comprises at least one vinyl monomer, wherein said coating encapsulates said metal oxide, and wherein said plurality of primary beads is distributed throughout said microporous matrix.

However, a microfluidic device comprising a matrix of a hydrophobic porous polymer covalently bonded to walls of a microchannel, with one or more magnetic beads covalently bonded to the hydrophobic porous polymer, has not been disclosed yet.

BRIEF SUMMARY OF THE INVENTION

The present invention provides a microfluidic device.

In one embodiment, the microfluidic device comprises an inlet and an outlet that are connected with each other through a microchannel, wherein a hydrophobic porous polymer is bonded to walls of the microchannel, and wherein a magnetic bead is bonded to the hydrophobic porous polymer. The invention also provides a method of making using the microfluidic device.

In an embodiment, method of making a microfluidic device, wherein a hydrophobic porous polymer is bonded to walls of a microchannel, comprises photopolymerizing a vinyl monomer; a magnetic bead having a vinyl group at the surface thereof; a cross-linkable monomer having two or more free radical polymerizable double bonds; a photopolymerization initiator; and a functional group having a free radical polymerizable vinyl double-bond, said functional group existing in a wall of a microchannel of a microfluidic device.

The invention also provides methods of using the microfluidic device.

DETAILED DESCRIPTION OF THE INVENTION

The invention will now be described more fully hereinafter with reference to the accompanying drawings, in which embodiments of the invention are shown. The invention may, however, be embodied in many different forms and should not be construed as limited to embodiments set forth herein. Rather these embodiments are provided so that this disclosure will be thorough and complete, and will fully convey the scope of the invention to those skilled in the art.

As used herein the term "cell" means a prokaryotic or eukaryotic cell, a plant cell, a bacterial cell, a pathogenic cell, a yeast cell, an aggregate of cells, a virus, or other nucleic acid-containing biological material, such as, for example, an organelle.

As used herein, the term "nucleic acid" means DNA or RNA. The DNA or RNA can be in any possible configuration, i.e. in the form of double-stranded (DS) nucleic acid, or in the form of single-stranded (ss) nucleic acid, or as a combination thereof (in part ds or ss).

As used herein, the term "cell binding" means the ability to bind a cell or other biomaterial, such as, for example a nucleic acid.

As used herein, the term "attaching" means the ability to attach or bind a cell or other biomaterial, such as, for example a nucleic acid, to a substrate.

As used herein, the term "microfluidic device" incorporates the concept of a microfluidic device that comprises microfluidic elements such as, e.g., microfluidic channels (also called microchannels or microscale channels). As used herein, the term "microfluidic" refers to a device component, e.g., chamber, channel, reservoir, or the like, that includes at lest one cross-sectional dimension, such as depth, width, length, diameter, etc. of from about 0.1 micrometer to about 1000 micrometer. Thus, the term "microchamber" and "microchannel" refer to a channel and a chamber that includes at lest one cross-sectional dimension, such as depth, width, and diameter of from about 0.1 micrometer to about 1000 micrometer, respectively.

In this application, the term "water contact angle" refers to water contact angle measured by a Kruss prop Shape Analysis System type DSA 10 Mk2. A droplet of 1.5 μl deionized water is automatically placed on the sample. The droplet was monitored every 0.2 seconds for a period of 10 seconds by a CCD-camera and analyzed by prop Shape Analysis software (DSA version 1.7, Kruss). The complete profile of the droplet was fitted by the tangent method to a general conic section equation. The angles were determined both at the right and left side. An average value is calculated for each drop and a total of five drops per sample are measured. The average of the five drops is taken the contact angle.

As used herein, the term "microchannel" is intended to encompass a microchannel or a microchamber.

In one embodiment, the invention provides a microfluidic device comprising an inlet and an outlet that are connected through a microchannel, wherein a hydrophobic porous polymer is bonded to a wall of the microchannel, and a magnetic bead is bonded to the hydrophobic porous polymer.

As used herein, a "microfluidic device" is a device comprising at least one inlet and at least one outlet which are connected with each other through a microchannel. Therefore, any device comprising an inlet and outlet which are connected through a microchannel is a microfluidic device, regardless of the name thereof. Exemplary microfluidic devices include, for example a microchip or a lab-on-a-chip. A lab-on-a-chip is an example of a microfluidic device that is generally used for concentrating cells, separating cells, disrupting cells, and amplifying nucleic acid. However, the microfluidic device of the invention need not be used as a lab-on-a-chip.

In one embodiment, the hydrophobic porous polymer of the invention can be a polymer for which the water contact angle is about 70 to about 90°, and which can concentrate materials such as cells by attaching the cells thereto. Examples of the hydrophobic porous polymers include a homopolymer, a copolymer, a cross-linked polymer, or any hydrophobic porous polymer known to one of skill in the art. In addition, the hydrophobic porous polymer can be cross-linked to form a network matrix.

In an embodiment, the hydrophobic porous polymer can be a polymer or a copolymer of vinyl monomers. A vinyl monomer has a vinyl double bond, and can be polymerized through a free radical polymerization reaction. Therefore, the vinyl monomer can include a monomer having an acryl group. The vinyl monomer can include, for example, a $C_1$-$C_{20}$ alkyl acrylate, a $C_1$-$C_{20}$ alkyl methacrylate a styrene, or a combination comprising at least one of the forgoing vinyl monomers, but is not limited thereto.

In addition, the hydrophobic porous polymer can be a cross-linked polymer of a vinyl monomer and a cross-linkable monomer. The cross-linkable monomer is not limited. For example, an aliphatic cross-linkable monomer or an aromatic cross-linkable monomer can be used. Exemplary aliphatic cross-linkable monomers include, an ethyleneglycol dimethacrylate, an ethyleneglycol diacrylate, a tri-methylol propane diacrylate, a tri-methylol propane triacrylate, a tri-methylol propane dimethacrylate, a tri-methylol propane trimethacrylate, a divinylketone, an arylacrylate, a diallyl maleate, a diallyl fumarate, a diallyl succinate, a diallyl carbonate, a diallyl malonate, a diallyl oxalate, a diallyl adipate, a diallyl sebacate, a divinyl sebacate, a N,N'-methylenediacrylamide, a N,N'-methylenedimethacrylamide, or combinations comprising at least one of the forgoing aliphatic cross-linkable monomers. Furthermore, the aromatic cross-linkable monomer can include a divinylbenzene, a trivinylbenzene, a divinyltoluene, a divinylnaphthalene, a diallylphthalate, a divinylxylene, or a divinylethylbenzene.

In one embodiment, the one or more magnetic beads can be covalently bonded to the hydrophobic porous polymer. The covalent bond between the hydrophobic porous polymer and the magnetic bead can be formed using any known method in the field, including, for example, by functionalizing the surface of the magnetic bead to have one or more vinyl double bonds, and carrying out an ion radical polymerization in the presence of the vinyl monomer and/or the cross-linkable monomer. In addition, the bond between the hydrophobic porous polymer and the wall of the microchannel may be a covalent bond, which can be formed using a conventional method. For example, the covalent bond between the hydrophobic porous polymer and the wall of the microchannel can be formed by synthesizing the hydrophobic porous polymer to which a magnetic bead is bonded, and reacting the hydrophobic porous polymer to a functionalized wall. Alternatively, the covalent bond between the hydrophobic porous polymer and the wall of the microchannel can be formed by functionalizing the wall of the microchannel to have a vinyl functional group which can be free radical polymerized, and then carrying out the free radical reaction in the microchannel.

The magnetic bead used in the present invention can be any conventional magnetic bead. Exemplary magnetic beads which can be used in the invention, include, for example, the magnetic beads disclosed in U.S. Pat. Nos. 5,395,688; 5,318,797; and 5,283,079, each disclosure of which is incorporated herein by reference.

According to one embodiment of the invention, the hydrophobic porous polymer in the microfluidic device is the product obtained from a photopolymerization reaction of a vinyl monomer; a magnetic bead having a vinyl group on the surface thereof; a cross-linkable monomer having two or more free radical polymerizable double bonds; a photopolymerization initiator; and a functional group having a free radical polymerizable vinyl double bond on the wall of the microchannel.

According to one embodiment of the invention, the photopolymerization reaction is carried out by injecting about 15 to about 33 parts by weight of the magnetic bead, about 25 to about 75 parts by weight of the cross-linkable monomer, and about 0.5 to about 1.3 parts by weight of the photopolymerization initiator based on 100 parts by weight of the vinyl monomer into the microchannel, and exposing the same to UV radiation.

According to the current embodiment of the invention, the vinyl monomer can be, for example, a $C_1$-$C_{20}$ alkyl acrylate, a $C_1$-$C_{20}$ alkyl methacrylate, a styrene, or combinations comprising at least one of the foregoing vinyl monomers. Exemplary cross-linkable monomers include, for example, an ethyleneglycol dimethacrylate, an ethyleneglycol diacrylate, a tri-methylol propane diacrylate, a tri-methylol propane triacrylate, a tri-methylol propane dimethacrylate, a tri-methylol propane trimethacrylate, a divinylketone, an arylacrylate, a diallyl maleate, a diallyl fumarate, a diallyl succinate, a diallyl carbonate, a diallyl malonate, a diallyl oxalate, a diallyl adipate, a diallyl sebacate, a divinyl sebacate, a N,N'-methylenediacrylamide, a N,N'-methylenedimethacrylamide, a tri-methylol propane trimethacrylate or combinations comprising at least one of the foregoing cross-linkable monomers.

According to the current embodiment of the present invention, the photopolymerization initiator can be, for example, a 2,2-dimethoxy-2-phenylacetophenone. In another advantageous embodiment, the microfluidic device according to the invention may further comprise a light-emitting device for providing light inside the microchannel. Any light-emitting device capable of emitting light can be used, so long as the light-emitting device is capable of emitting light in the wavelength range that can be absorbed by the magnetic bead. The light-emitting device can be, for example, a laser or a UV crosslinker. The light-emitting device, can be located inside or outside the microchannel so long as the light can be applied to the hydrophobic porous polymer or to the magnetic bead bonded to the hydrophobic porous polymer within the microchannel. When the light-emitting device is located outside the microchannel, it can be attached to, or detached from (separate from) the microchannel, and at least one wall of the microchannel is made from a light-transparent material. The light-emitting device can be attached to, or detached from (separate from) the microfluidic device.

In one embodiment, the light-emitting device, for example, a laser, can be used to apply a laser beam to the one or more magnetic beads, causing the one or more magnetic beads to heat and disrupt cells in samples and denature biological material such as a protein.

In another embodiment, the microfluidic device according to the invention can further comprise a means for performing a Polymerase Chain Reaction (PCR) reaction. The means comprises a reaction chamber which is in fluid communication with the microchannel, a heater which supplies heat to the reaction chamber, and a cooler which dissipates the heat (i.e., which cools the reaction chamber). Therefore, according to the current embodiment, the microfluidic device can concentrate and disrupt biological samples containing cells in the microchannel, and carry out PCR directly using the obtained cell lysates.

In one embodiment, the invention provides a method of concentrating cells within the microchannel of the microfluidic device described herein, the method comprising, attaching cells to the hydrophobic porous polymer bonded to the wall of the microchannel by flowing a sample containing the cells through the microchannel of the microfluidic device according to the invention.

Since the hydrophobic porous polymer is bonded to the microchannel, cells attach to the hydrophobic porous polymer and are thereby concentrated within the microchannel. The sample containing cells has a pH value of about 2.0 to about 7.0, and preferably about 2.5 to about 4.0.

According to another embodiment, the invention provides a method of disrupting cells. The method comprises attaching cells to the hydrophobic porous polymer bonded to the walls of the microchannel by flowing a sample containing cells through the microchannel of the microfluidic device according to the present invention, wherein the microfluidic device further comprises a light-emitting device for providing light inside the microchannel; and disrupting cells by generating heat by exposing the hydrophobic porous polymer in the microchannel to the light.

According to the current embodiment other light emitted is within the wavelength range which the one or more magnetic beads can absorb. Furthermore, the light-emitting device can be any light-emitting device capable of emitting light within the wavelength range which the magnetic bead can absorb. An exemplary light-emitting device includes, for example, a laser generator.

In one embodiment, the method of disrupting cells according to the invention comprises attaching cells to the hydrophobic porous polymer bonded to the microchannel by flowing a sample containing cells through the microchannel of the microfluidic device according to the invention.

According to the current embodiment the method of disrupting cells comprises disrupting the cells by generating heat by exposing the hydrophobic porous polymer in the microchannel to light. Thus, according to one embodiment, the light-emitting device emits light, for example, laser light, which is applied to the hydrophobic porous polymer and to any magnetic beads bonded to the hydrophobic porous polymer to generate heat. The heat generated functions to disrupt the cells.

According to another embodiment, the invention provides a method of amplifying target nucleic acid from cells, comprising: attaching cells to the hydrophobic porous polymer by flowing a sample containing cells through the microchannel of the microfluidic device according to the invention. In some embodiments, the microfluidic device further comprises a light-emitting device for providing light inside the microchannel and a means for performing a PCR reaction comprising: a reaction chamber which is in fluid communication with the microchannel; a heater which supplies heat to the reaction chamber; and a cooler which dissipates the heat. The method further comprises disrupting cells by generating heat by exposing the hydrophobic porous polymer and magnetic beads in the microchannel to light; and performing PCR using the lysates of the disrupted cells as a source for template DNA.

In an exemplary embodiment, the light emitted from the light-emitting device is in a wavelength range which the magnetic bead can absorb. Further, the light-emitting device can be any light-emitting device capable of emitting light in the wavelength range which the magnetic bead can absorb. The light-emitting device can be, for example, a laser generator.

For the current embodiment of the invention the method of amplifying target nucleic acid from cells comprises: attaching cells to the hydrophobic porous polymer by flowing a sample containing cells through the microchannel of the microfluidic device according to the present invention; and disrupting cells by generating heat by exposing the hydrophobic porous polymer in the microchannel to light. Each of these processes is described above.

In another embodiment, the method of amplifying the target nucleic acid from cells also comprises performing a PCR using the lysates of the cells as a source of template DNA. Polymerase Chain Reaction (PCR) is well known in the field, and is disclosed in detail in U.S. Pat. Nos. 4,683,195; 4,683,202; and 4,965,188, each disclosure of which is incorporated herein by reference. PCR relates to hybridization of a primer to a target DNA, which is also referred to as a "template". Under the appropriate conditions, the primers hybridize or anneal to the target DNA in the presence of a polymerase such as, for example, a DNA polymerase, and dNTP molecules. Next the DNA polymerase generates a copy of the template DNA extending from the primer in a process called elongation or extension. Extension of the copy DNA molecule starts at the annealed primer and works its way along the template DNA strand, preparing a copy of the template DNA. Following extension, a double stranded primer extension product is formed. The primer extension product can then be denatured, producing one copy of the template DNA. Once the double stranded DNA molecule has been denatured, the process of annealing, extension, and denaturation can be repeated generating multiple copies. Thus, the amount of DNA having the same sequence as the target DNA exponentially increases by carrying out multiple cycles of annealing, extension, and denaturation.

The PCR in the method of amplifying the target nucleic acid from the cells is carried out in the means for performing the PCR reaction within the microfluidic device.

The present invention will be described in more detail with reference to the following examples. These examples are provided for illustrative purposes only and are not intended to limit the scope of the present invention.

EXAMPLES

Example 1

Synthesis of a Hydrophobic Porous Polymer which is Copolymerized with Functional Groups on Magnetic Beads and the wall of a Microchamber in a Microfluidic Device For this example, a microchamber having a volume of 6.0 of was manufactured in a microchip for TMC-1000 (Samsung Techwin) by bonding wet-etched silicon and glass having pores. In this example, a microchamber was formed and used, however the procedures are also applicable to formation and use of microchannels. Magnetic beads and the surface of the microchamber were reacted with 3-(trimethoxysilyl)propyl methacrylate to form vinyl functional groups on the surface of the magnetic beads and the surface of the microchamber. Then, the magnetic beads, butylmethacrylate as a vinyl monomer, trimethylolpropane trimethacrylate as a cross-linkable monomer, and 2,2-dimethoxy-2-phenylacetophenone as a photopolymerization initiator were photopolymerized within the microchannel by irradiating the microchannel with ultraviolet (UV) light to manufacture a microchannel having a polymerized polybutylmethacrylate covalently bonded to the magnetic beads and to the walls of the microchamber.

(1) Methacrylate Functionalization of a Magnetic Bead 1 ml (40 mg) of magnetic beads (BIOCINE Corporation, radius of 1 μm) having a silicon oxide surface were added to a microtube, and washed three times with 0.1 N NaOH, once with distilled water, three times with 0.1 N HCl, once with distilled water, and three times with acetone. The magnetic beads were separated from the solution using a magnet. The magnetic beads were then reacted with 30% 3-(trimethoxysilyl)propyl methacrylate solution (v/v, acetone) by mixing well for 12 hours. After the reaction ended, the reaction solution was washed three times with acetone, three times with methanol, and the magnetic beads were suspended and stored in 1 ml of methanol.

(2) Methacrylate Functionalization of Inner Surface of the Microchamber 0.1 N NaOH was added to a microchamber (volume 6,0) of a microchip for TMC-1000 (Samsung Techwin) and maintained for 20 minutes. Then, the solution was removed from the microchamber and the microchamber was washed with water. 0.1 N HCl was added to the microchamber and maintained for 20 minutes. Then, the solution was removed from the microchamber and the microchamber was washed with water and acetone respectively.

After the microchamber was dried, a 30% 3-(trimethoxysilyl)propyl methacrylate solution (v/v, acetone) was added thereto and maintained at room temperature for 12 hours. Then, the solution was removed from the microchamber and the microchamber was washed three times with acetone, and dried in an oven.

(3) Synthesis of Butylmethacrylate Copolymer

A reactant solution containing 15 weight % of butylmethacrylate, 10 weight % of trimethylolpropane trimethacrylate (TRIM), 50 weight % of methanol, and 25 weight % of hexane was prepared, and 10 mg of 2,2-dimethoxy-2-phenylacetophenone was dissolved therein.

100 μl of the methacrylate-functionalized magnetic beads were removed from the methanol solution generated in (1) using a magnet, and then were added to the reactant solution and mixed well. This reactant solution was injected into the methacrylate-functionalized microchamber prepared in (2), and exposed to a light having a wavelength of 254 nm at an energy of 5000 mJ/cm$^2$ for 4 minutes using a UV-cross-linker (CL-1000). The reactant solution was removed by centrifuging the chip itself, and the reaction product formed on the microchamber surface was washed three times with methanol and dried in an oven. As a control, a polymer without magnetic beads was synthesized in the same manner as described above, except the process of adding and mixing the methacrylate-functionalized magnetic beads was omitted.

Figure 1:
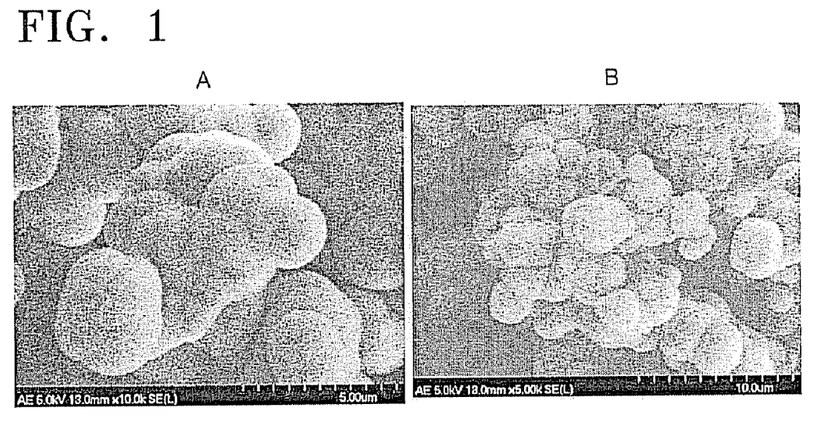
FIG. 1 provides Scanning Electron Microscope (SEM) images of magnetic beads bonded to a polybutylmethacrylate in a microchannel, according to an embodiment of the invention.

FIG. 1 provides SEM images showing the polymerized polybutylmethacrylate to which the magnetic beads synthesized in a microchamber are bonded. As shown in FIG. 1, many pores exist in the polymerized polybutylmethacrylate bonded to the microchamber and magnetic beads.

Example 2

Cell Concentrating Microchip which comprises a Microchamber with a Hydrophobic Porous Polymer Bonded to Magnetic Beads and the Microchamber For this example, cells were concentrated by flowing a sample containing cells through a microchamber which comprises a polymerized polybutylmethacrylate which is bonded to magnetic beads and the microchamber.

First, E. coli was added to 100 mM phosphate buffer (pH 4.0) to make a 0.01 $OD_{600}$ solution. The E. coli solution was flowed into a microchamber with polybutylmethacrylate bonded to the microchamber walls and to magnetic beads prepared according to Example 1 at a rate of 50 μl/min for 3 minutes. Before and after flowing through the microchamber, samples of the E. coli solution were diluted 10,000 times with a 1×PBS, and smeared on 3M PetriFilm, which is used for cell culture in order to determine cell concentration. Then, the cell concentrations of the E. coli solutions before and after flowing through the microchamber, were measured by counting the number of E. coli colonies grown on the 3M PetriFilm. Based on the measurement, the binding ratio, that is, the ratio of E. coli that were bonded to polymers in the microchamber with regard to the E. coli cells in the initial solution that entered the microchamber was calculated by comparing the number of cells before and after flowing through the microchamber, and then a concentration ratio was calculated by comparing the volume of solution flowing through the microchamber and the volume of the microchamber. As a control group, cells were concentrated by flowing a sample containing cells in a microchamber with polybutylmethacrylate bonded to the microchamber walls but lacking bonded magnetic beads (Polymer Only). The results are shown in Table 1.

TABLE 1

|  | Polymer-magnetic bead | Polymer Only |
|---|---|---|
| Concentration ratio * | 13.0(±2.7) | 14.3(±0.9) | where concentration ratio=binding ratio×input volume/microchamber volume.

As shown in Table 1, *E. coli* was concentrated more than about 10 times whether or not magnetic beads were bonded.

Example 3

Cell Concentrating, Cell Disrupting and PCR using the Cell Lysates in a Microchamber with a Hydrophobic Porous Polymer Bonded to the Microchamber Walls and to Magnetic Beads For this example, the *E. coli* which was concentrated in Example 2 was disrupted (lysed) using a laser, and then PCR was performed using the lysates of the cells to provide template DNA to amplify DNA of *E. coli*. PCR was also performed using lysates of cells concentrated according to the control of Example 2 to provide a template DNA to amplify DNA of *E. coli* (Polymer Only).

First, *E. coli* cells were concentrated according to Example 2. The solution was removed from the microchamber, and Tris (10 mM, pH 9.0) or 1×PBS (phosphate buffered saline) solution (the "disrupting buffer") was filled therein. Then, the polymer bonded magnetic beads were exposed to laser light having a wavelength of 808 nm through the top substrate of the microchamber using a laser generator (Hamamatsu 8446-72 Corporation, 1W) for 40 seconds. The resulting cell lysates were directly used for PCR.

A PCR master mixture comprising 20 µl of 10× Solgent buffer, 4.0 of Tag polymerase (Solgent), 4 µl of dNTP (10 mMm, Solgent), 10 µl each of 10 µM forward primer and 10 µM reverse primer (SEQ ID Nos: 1 and 2, respectively) and 8 µl of TagMan™ probe (10 µM) (SEQ ID NO: 3) (total 56 0) was mixed at a ratio of 3:1 (v/v) with the cell lysates removed from the microchamber. A volume of 1 µl of the resulting mixture was injected into a reaction chamber of TMC-1000, and PCR was carried out.

The PCR was carried out at 95° C. for 1 minute for a denaturation, and for 5 seconds at 95° C., for 20 seconds at 45° C., and for 20 seconds at 72° C., and repeated 40 times. Ct was measured concurrently while carrying out real-time PCR. The real-time PCR results are shown in Table 2.

TABLE 2

| Disruption Buffer | Polymer-magnetic bead | Polymer Only | Before concentration |
|---|---|---|---|
| PBS | 26.81 | 31.23 | 30.19 |
| Tris | 22.50 | 25.90 | — |

As shown in Table 2, Ct was decreased when lysates from a polymer-magnetic bead microchamber was used compared to lysates from the polymer only microchamber. The reason for this is believed to be that cell disrupting by a laser light is more efficient in the presence of magnetic beads. Ct value represents the number of cycles at which detectable fluorescence signals are detected in a real-time PCR. That is, the higher an initial concentration of DNA is, the more fluorescence signals can be detected at a low Ct value.

The PCR products were subjected to an electrophoretic analysis, and the resulting products were analyzed using a LabChip (Agilent Corporation). Results of the analysis are shown in Table 3.

TABLE 3

| Lane | Polymer type | buffer | DNA concentration (ng/µl) |
|---|---|---|---|
| 1 | Polymer-magnetic bead | Tris | 8.1 |
| 2 | Polymer only | Tris | 1.4 |
| 3 | Polymer-magnetic bead | PBS | <0.5 |
| 4 | Polymer only | PBS | <0.5 |

As shown in Table 3, a greater amount of PCR product resulted from lysates obtained from a microchamber which comprises a polybutylmethacrylate bonded to magnetic beads and the microchamber walls and when Tris buffer was used as the disrupting buffer. These results are consistent with the Ct values shown in Table 2. On the other hand, only a minimal amount of the PCR product was produced and only primer dimers existed when PBS buffer was used as the disrupting buffer, which is inconsistent with the Ct value. Without being bound by theory, it is believed that amplification was more efficient when Tris was used as the disrupting buffer because when PBS buffer was used, the DNA was attached to the surface of the polymer after cell disrupting.

Figure 2:
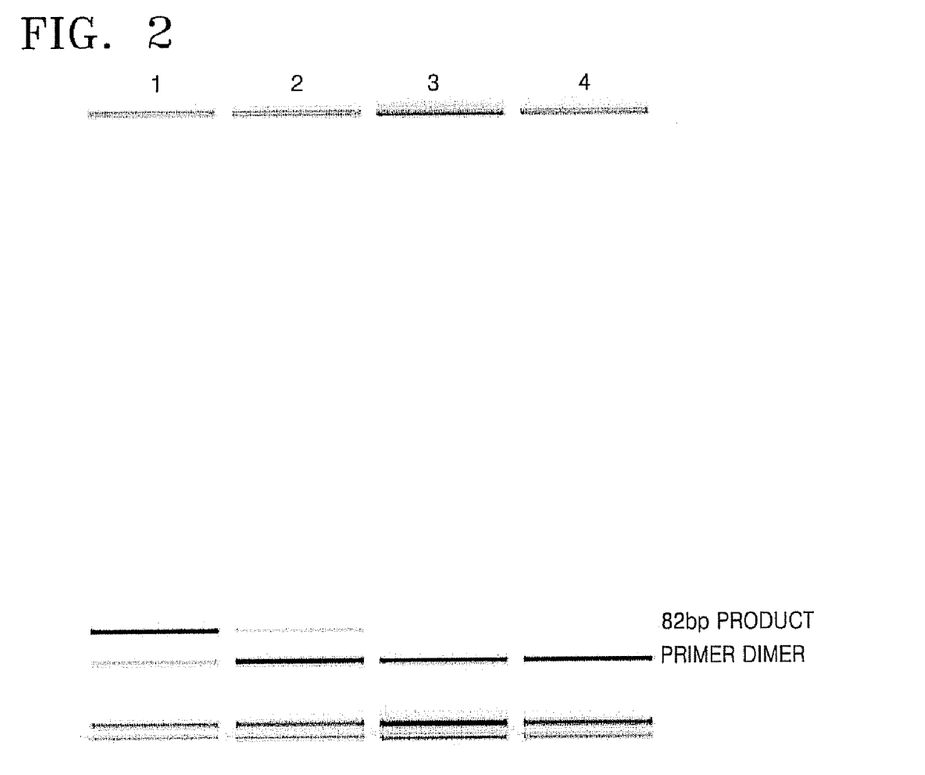
FIG. 2 is an image showing the results of an electrophoretic analysis of PCR products obtained according to an embodiment of the invention.
Figure 3:
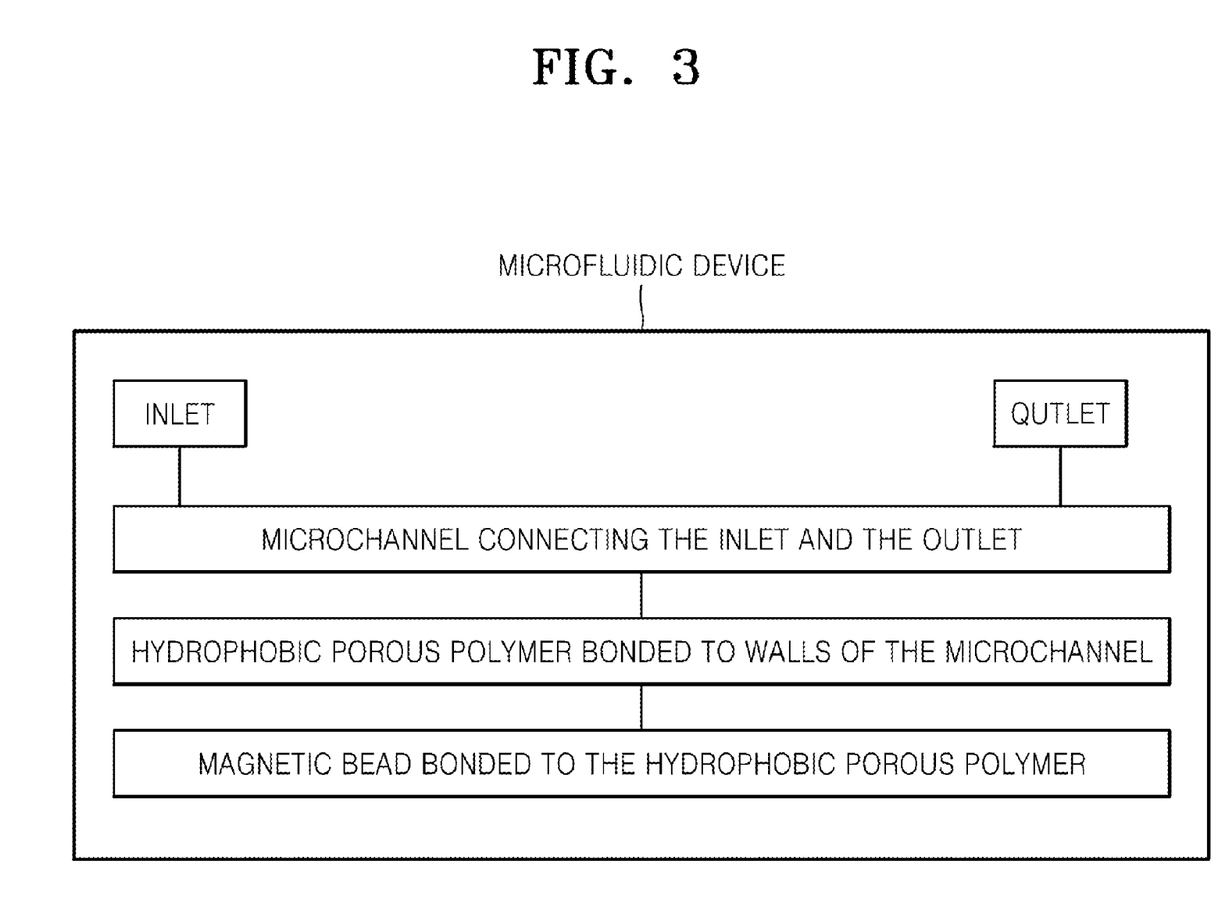
FIG. 3 is a schematic diagram showing one example of the claimed device.

FIG. 2 is an image of electrophoresis results of the PCR products obtained above, wherein *E. coli* cells were concentrated within a microchamber, comprising a hydrophobic porous polymer bonded to magnetic beads and the microchamber walls. The *E. coli* cells were disrupted using a laser and PCR was carried out using the cell lysates, as prepared above, directly to provide template DNA. The samples added to each lane of the electrophoresis gel correspond to what is shown in Table 3 above.

As demonstrated above, the present invention provides that at least one process of concentrating cells, disrupting cells, and amplifying nucleic acid from the cells can be carried out efficiently using the microfluidic device according to the present invention.

Further, the above disclosure also demonstrates that cells can be efficiently concentrated in the microchannel using the method of concentrating cells in the microchannel according to the present invention.

The above disclosure also demonstrates that cells can be efficiently disrupted in the microchannel using the method of disrupting cells according to the present invention.

The above disclosure also demonstrates that a target nucleic acid can be efficiently amplified using the method of amplifying a target nucleic acid from cells according to the present invention.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microfluidic device comprising
   an inlet and an outlet that are connected with each other through a microchannel,
   a hydrophobic porous polymer is bonded to walls of the microchannel, wherein the water contact angle of the hydrophobic porous polymer is about 70 to about 90°, and
   a magnetic bead is bonded to the hydrophobic porous polymer.

2. The device of claim 1, wherein the hydrophobic porous polymer is a polymer of vinyl monomers.

3. The device of claim 2, wherein the vinyl monomers are selected from the group consisting of a $C_1$-$C_{20}$ alkyl acrylate, a $C_1$-$C_{20}$ alkyl methacrylate, a styrene, and combinations comprising at least one of the foregoing, vinyl monomers.

4. The device of claim 1, wherein the hydrophobic porous polymer is a cross-linked hydrophobic porous polymer.

5. The device of claim 4, wherein the hydrophobic porous polymer is cross-linked by an aliphatic cross-linkable monomer.

6. The device of claim 5, wherein the aliphatic cross-linkable monomer is selected from the group consisting of an ethyleneglycol dimethacrylate, an ethyleneglycol diacrylate, a tri-methylol propane diacrylate, a tri-methylol propane triacrylate, a tri-methylol propane dimethacrylate, a tri-methylol propane trimethacrylate, a divinylketone, arylacrylate, diallyl maleate, diallyl fumarate, diallyl succinate, diallyl carbonate, diallyl malonate, diallyl oxalate, diallyl adipate, diallyl sebacate, divinyl sebacate, N,N'-methylenediacrylamide, N,N'-methylenedimethacrylamide, and combinations comprising at least one of the foregoing aliphatic cross-linkable monomers.

7. The device of claim 4, wherein the hydrophobic porous polymer is cross-linked by an aromatic cross-linkable monomer.

8. The device of claim 7, wherein the aromatic cross-linkable monomer is selected from the group consisting of a divinylbenzene, a trivinylbenzene, a divinyltoluene, a divinylnaphthalene, a diallylphthalate, a divinylxylene, a divinylethylbenzene, and combinations comprising at least one of the foregoing aromatic cross-linkable monomers.

9. The device of claim 1, wherein the magnetic bead is covalently bonded to the hydrophobic porous polymer.

10. The device of claim 1, further comprising a light-emitting device, wherein the light-emitting device provides light to the inside the microchannel.

11. The device of claim 1, further comprising a means for performing a PCR reaction, the means comprising:
    a reaction chamber which is in fluid communication with the microchannel;
    a heater which provides heat to the reaction chamber; and
    a cooler which dissipates the heat.

12. The device of claim 1, wherein the microchannel is a microchamber.

13. A method of concentrating cells, comprising
    attaching cells to a hydrophobic porous polymer bonded to walls of the microchannel of the microfluidic device of claim 1 by flowing a sample containing the cells through the microchannel.

14. The method of claim 13, wherein the sample containing the cells has a pH of about 2.0 to about 7.0.

15. A method of disrupting cells, comprising:
    attaching cells to a hydrophobic porous polymer bonded to walls of a microchannel of a microfluidic device of claim 1, by flowing a sample containing the cells through the microchannel of the microfluidic device; and
    disrupting the cells by generating heat by exposing the hydrophobic porous polymer in the microchannel to light from a light-emitting device for providing light inside the microchannel.

16. A method of amplifying a target DNA from cells, comprising:
    attaching cells to a hydrophobic porous polymer bonded to walls of a microchannel of a microfluidic device by flowing a sample containing the cells through the microchannel of the microfluidic device of claim 1,
    wherein the microfluidic device of claim 1 further comprises:
      a light-emitting device for providing light inside the microchannel; and
      a means for performing a PCR reaction comprising:
        a reaction chamber which is in fluid communication with the microchannel;
        a heater which supplies heat to the reaction chamber; and
        a cooler which dissipates the heat from the reaction chamber;
    lysing the cells by generating heat by exposing the hydrophobic porous polymer in the microchannel to light emitted from the light emitting device; and
    performing PCR using a target DNA present in the cell lysates.

17. The method of claim 15, wherein the PCR is carried out in the means for performing a PCR reaction in the microfluidic device.

* * * * *